United States Patent [19]

Hamerlinck

[11] 4,437,353

[45] Mar. 20, 1984

[54] PRESSURIZED CONTAINER TESTING APPARATUS

[76] Inventor: R. Dean Hamerlinck, 620 Pope St., St. Helena, Calif. 94574

[21] Appl. No.: 375,999

[22] Filed: May 7, 1982

[51] Int. Cl.³ .............................................. G01N 1/22
[52] U.S. Cl. ............................... 73/863.81; 73/864.74
[58] Field of Search ................... 73/52, 863.81, 863.86, 73/864.74; 81/3.2, 3.31, 3.32

[56] References Cited

U.S. PATENT DOCUMENTS

| | | | |
|---|---|---|---|
| 1,539,937 | 6/1925 | Cochrane | 73/52 |
| 2,393,552 | 1/1946 | Morpeth | 73/52 |
| 3,958,448 | 5/1976 | Willis et al. | 73/52 |

FOREIGN PATENT DOCUMENTS 17134  6/1901  Sweden ............................ 81/3.31

Primary Examiner—S. Clement Swisher
Attorney, Agent, or Firm—Mark C. Jacobs

[57] ABSTRACT

Apparatus for piercing a cork of a liquid containing bottle with a hollow needle, the eye of the needle terminating below the cork in the bottle and above the liquid contents therein. The apparatus is adapted to align the bottle so that the needle can pierce the cork in a straight downward direction and air measuring apparatus may be coupled to the needle to detect the presence or absence of air or other gases in the bottle.

11 Claims, 11 Drawing Figures

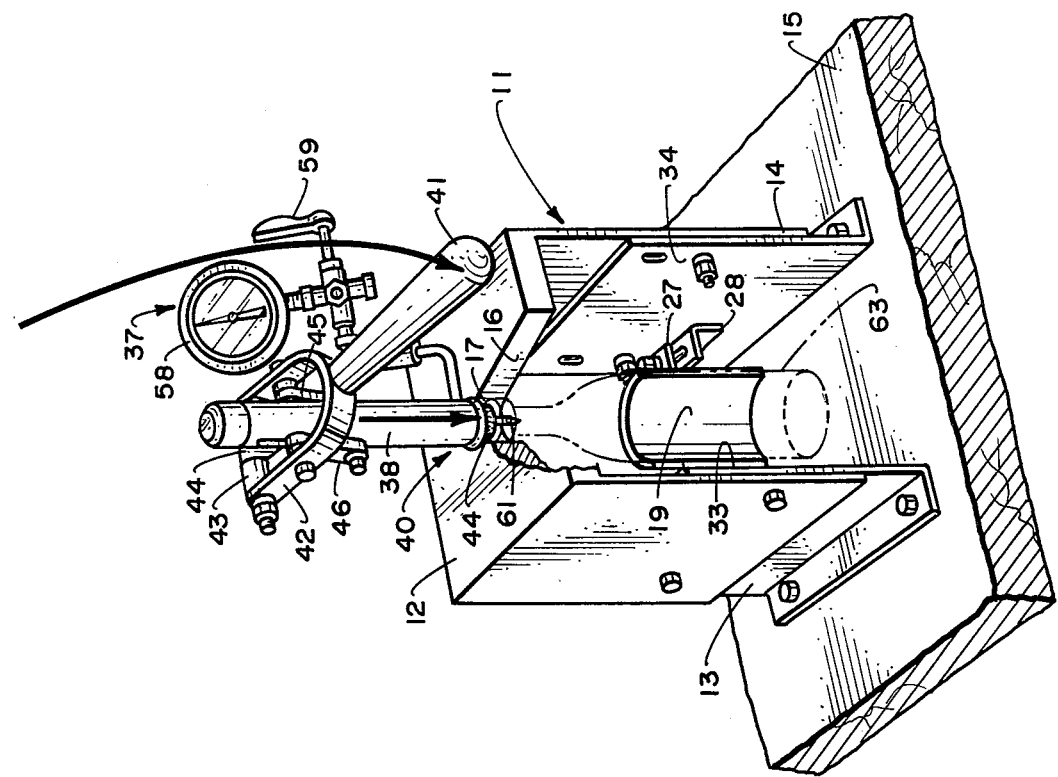
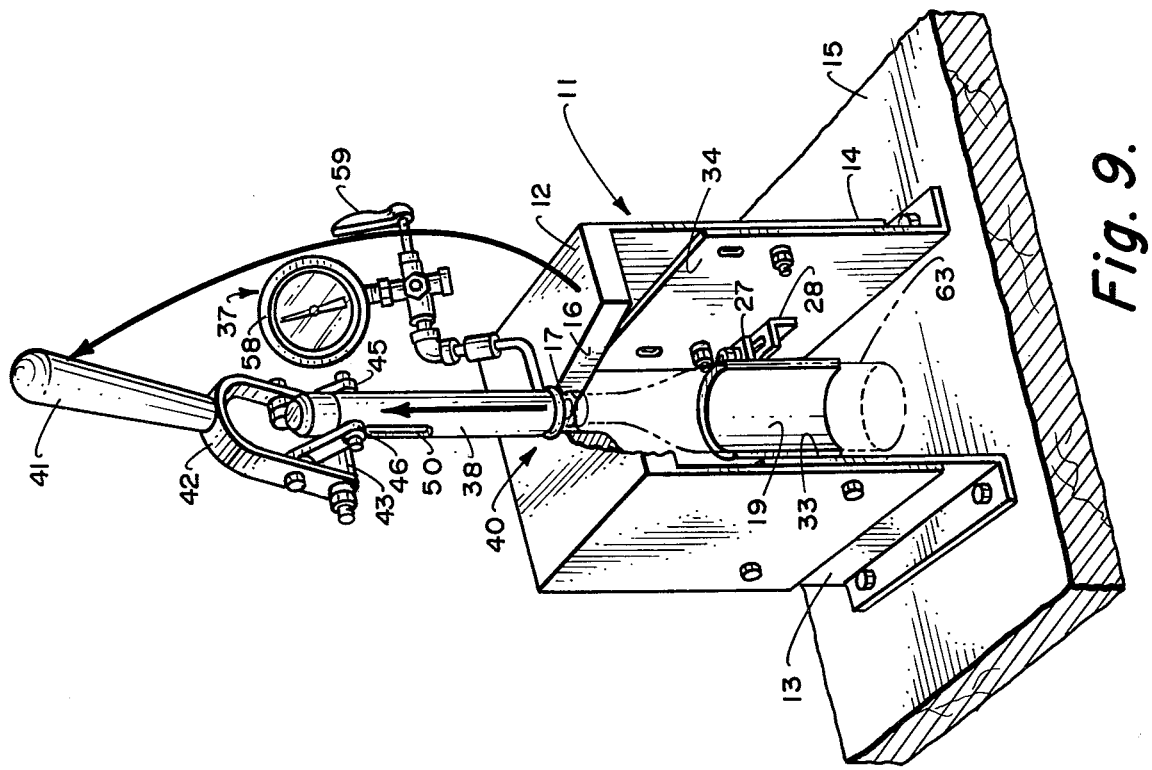

PRESSURIZED CONTAINER TESTING APPARATUS

BACKGROUND OF THE INVENTION

1. Field of the Invention

The invention relates to testing apparatus; and, more particularly, to apparatus for detecting the amount of air present in a previously pressurized container. Other gases are also detected.

2. Description of the Prior Art

Normally, in a wine packaging process, an assembly line is used to move a plurality of empty wine bottles past stations where they are filled with wine, then to a corking station where corks are placed in the open bottle tops to seal the same. Prior to such corking, the liquid contents of the bottle are depressurized to remove all air or gases from the bottle which air is detrimental both to the quality of the wine and the efficiency of the seal. High quality wineries desire to have no air at all present in their wines after corking. In addition to the quality of the wine, there has been an increase in leakage and accidents caused by bottles exploding after pressurizing and corking due to residual pressurized gases being present in the bottles where it was thought there were no gases. The bottles would thus break, leak and, when inverted, pressure would drive the wine out of the bottle or force a passageway to open slowly in the side of the cork since the cork is fresh and hadn't yet hardened. Such air, being present in the wine, even if pressurized, will affect the quality of the wine.

In order to check on the quality of the vacuum process, which step is carried out almost instantaneously prior to corking, various techniques have been suggested to determine if the right amount of vacuum is being pulled from the bottles. For example, in one technique, an empty bottle is run through the vacuum forming process and corked without any liquids contents therein. If the vacuum forming apparatus has a plurality of different vacuum-forming heads, which can clog up due to cork dust or the like, empty bottles must be tested for each head. This of course is quite time consuming and cannot be done manually since it is difficult to pierce a cork with a needle or the like manually. Also, the needle must be large enough to be easily inserted (which large sized needle might collapse or otherwise break the cork) yet not too delicate or it will break.

Various prior art devices, such as those disclosed in U.S. Pat. Nos. 1,211,942; 4,208,903 and 1,539,937 have been suggested in the past but have proven unsatisfactory for use in today's assembly line filling techniques. For example, in U.S. Pat. No. 4,208,903, the complicated machine actually shakes a heavily carbonated liquid since it is desired to measure the degree of carbonization, directly opposite of what is desired in the wine industry.

There is thus a need for apparatus for quickly and easily determining if there is any air present in a previously pressurized corked liquid-containing bottle.

The term air as used herein is intended to include all of the gases that may be present in a bottle of wine, champagne or sparkling wine, namely $CO_2$, $N_2$, $O_2$ and the like.

SUMMARY OF THE INVENTION

It is an object of this invention to provide improved apparatus for detecting the presence of air or other gases in a previously pressurized and sealed liquid filled container.

It is another object of this invention to carry out the foregoing object on bottles of various sizes and shapes.

It is a further object of this invention to provide such apparatus for piercing a cork of a corked wine bottle to detect the pressure or absence of air therein.

It is still another object of the invention to provide apparatus for inserting a sharp hollow needle downwardly in a straight vertical line through a cork and into a bottle with the eye of the needle terminating in a space above the liquid contents in said bottle but below the bottom of the cork.

These and other objects are preferably accomplished by providing a hollow needle, the eye of the needle terminating in a point and adapted to be moved downwardly to pierce a cork of a wine bottle or the like, the eye terminating below the bottom of the cork but above the liquid in the bottle. The apparatus is adaped to align the bottle so that the needle can pierce the cork in a downward direction and air measuring means may be coupled to the needle to detect the presence or absence of air or other gases in the bottle.

BRIEF DESCRIPTION OF THE DRAWING

FIG. 9 is a perspective view illustrating the operation of the apparatus of FIGS. 1 to 10 showing a bottle in position prior to piercing the cork thereof; and FIG. 10 is a perspective view similar to FIG. 9 showing the position of the bottle and apparatus after piercing of the cork.

DESCRIPTION OF THE PREFERRED EMBODIMENT

Figure 1:
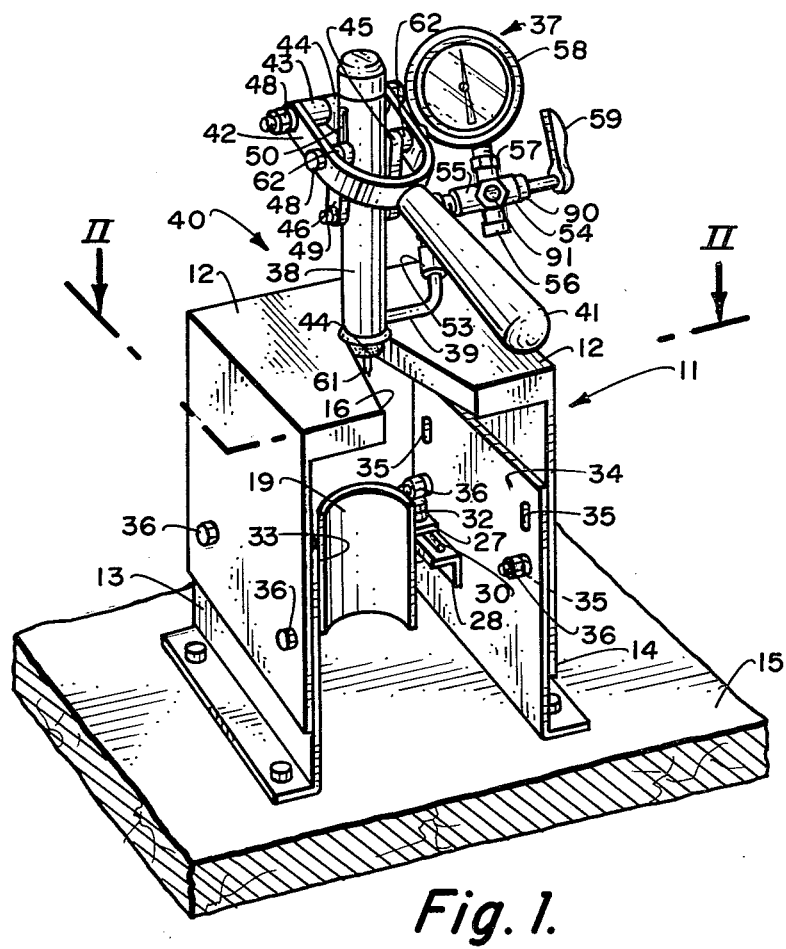
FIG. 1 is perspective view of apparatus in accordance with the invention.

Referring now to FIG. 1 of the drawing, apparatus 10 is shown in accordance with the teachings of the invention comprising a housing 11 preferably having at least a top wall 12 and interconnected spaced vertical side walls 13,14. Obviously, housing 11 may be mounted on any suitable supporting surface, such as surface 15, which surface may be part of a bottle filling assemby line.

Figure 2:
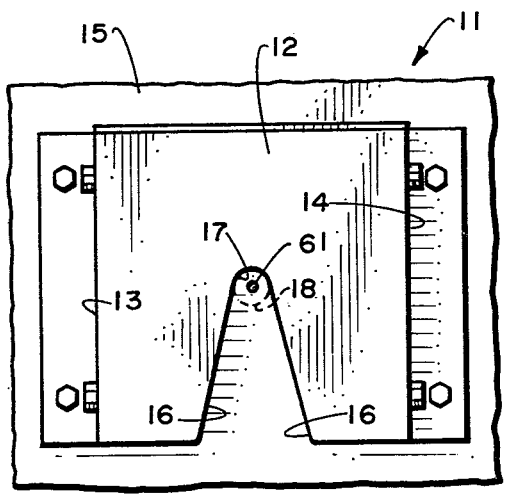
FIG. 2 is a view taken along lines II—II of FIG. 1.

Apparatus 10 further includes a bottle neck guide means in the form of a tapered generally V-shaped slot 16 in top wall 12 having a curved apex 17 (FIG. 2) of a suitable size for receiving the top of the neck of a bottle (e.g., neck 18 shown in dotted lines) which abuts against apex 17.

Figure 3:
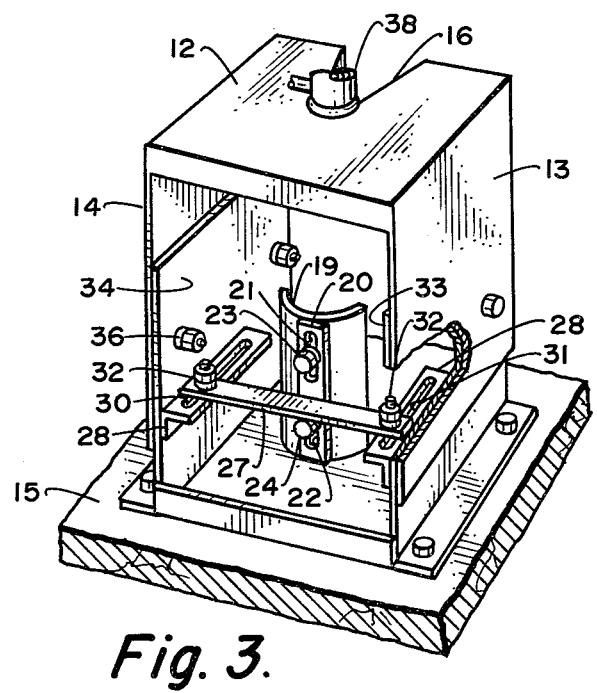
FIG. 3 is a rear perspective view of a portion of the apparatus of FIG. 1.

Apparatus 10 also includes a bottle guide support 19 which may be in the form of a curved shield of any suitable material, such as metal or plastic mounted internally of housing 11. Support 19 may be mounted in any suitable manner and is preferably both vertically and horizontally adjustable. Thus, as shown in FIG. 3, support 19 is welded or otherwise secured on the back thereof is a vertical plate 20 having a pair of vertically aligned elongated apertures 21,22 with threaded bolts 23,24, respectively, extending from the rear of support 19 through aperture 21,22. Nuts 25,26 are threaded onto bolts 23,24 to retain support 19 in position. Since apertures 21,22 are elongated, vertical adjustment of support 19 is possible.

An elongated flat cross-bar 27 is welded or otherwise secured to plate 10 at generally the midpoint thereof and extends between side walls 13,14, as shown, terminating in apertured ends. A apir of flat support plates 28,29 are welded or otherwise secured on the inside of each side wall 13,14, each plate 28,29 having an elongated slot 30,31. A suitable nut and bolt 32 passing through the apertures in the ends of cross-bar 27 and slots 30,31 fixedly secures the cross-bar 27 to plates 28,29. Since slots 30,31 are elongated, support 19 is horizontally adjustable. The horizontal and vertical adjustment provided allows support 19 to be adjusted to compensate for testing bottles of varying dimensions.

Top wall 12 may have a pair of downwardly extending wall panels 33,34 telescopingly fitting over side walls 13,14 with longitudinal slots 35, such as two spaced slots on each side wall 13,14, in side walls 13,14. Suitable nuts and bolts 36 secure wall panels 33,34 to its respective side wall 13,14. However, longitudinal slots 35 permit vertical adjustment of top wall 12 so apparatus 10 can be readily accomodated to bottles of differing heights.

Figure 4:
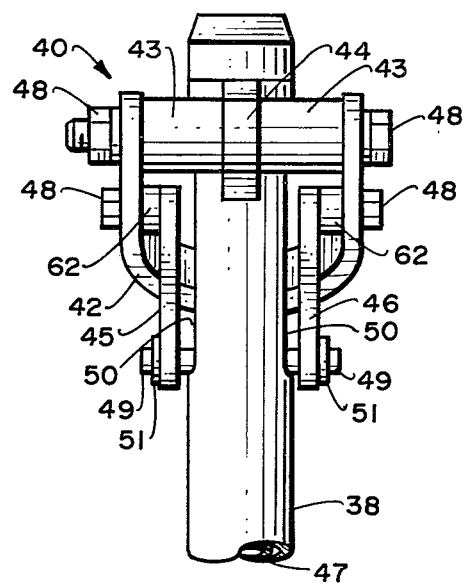
FIG. 4 is a rear vertical view of a portion of the apparatus of FIG. 3.

The pressure measuring means 37 of the invention will now be described. Means 37 includes a vertical piston cylinder 38 having an air inlet 39 at its lower end and an actuating lever 40 pivotally mounted at its upper end. Lever 40 includes a handle portion 41 connected to a U-shaped yoke portion 42 straddling therebetween the upper end of cylinder 38. The free ends of yoke portion 42 are interconnected by a cylindrical sleeve 43 (FIG. 4) secured to and rotatable within a collar 44 mounted on cylinder 38.

Figure 5:
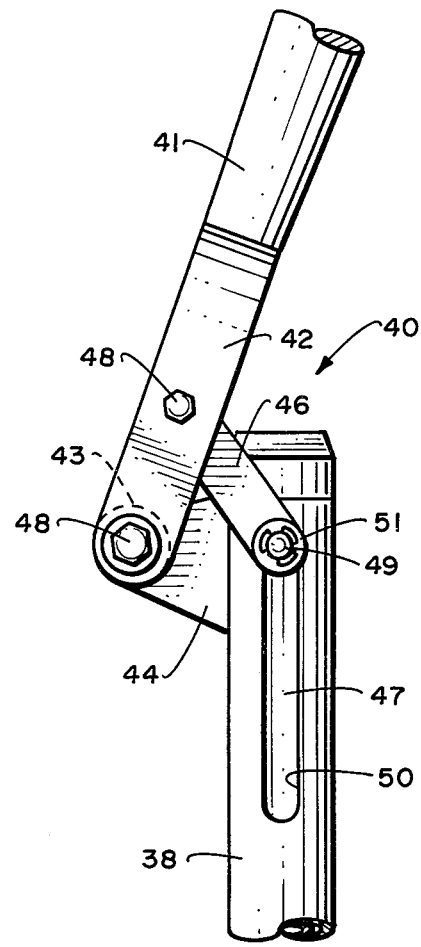
FIG. 5 is a side view of FIG. 4 but in up position.

As shown in FIGS. 1 and 5, a pair of links 45,46 are pivotally connected at one end to a midpoint on the arms of yoke portion 42 by a nut and bolt 48 and the other end to the top of a piston 47 slidably mounted internally of cylinder 38. A pin 40, coupled to piston 47 and passing through an elongated slot 50 in cylinder 38, is connected to each link (such as link 46 in FIG. 5) by a lock nut 51. It can be appreciated that movement of yoke portion 42 up and down also moves links 45,46 thereby moving piston 47 up and down within cylinder 38. As seen in FIG. 1, spacers 62 may be provided between links 45,46 and the inner arms of yoke portion 42.

Figure 6:
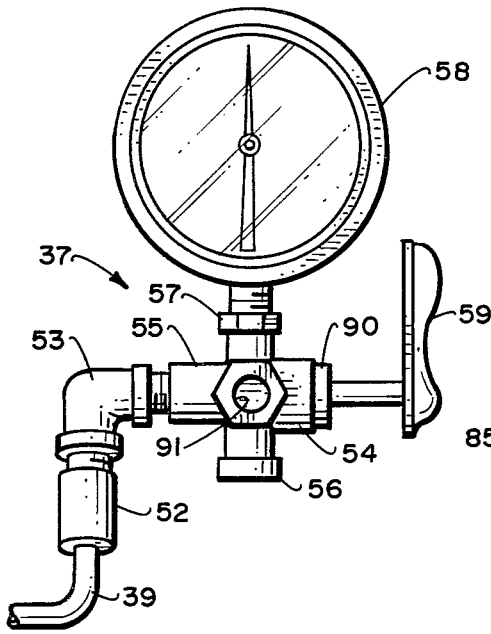
FIG. 6 is a detailed view of a portion of the apparatus of FIG. 1.

Air inlet 39 (see also FIG. 6) is coupled to a fitting 52 coupled to elbow 53 which is in turn coupled to one port 55 of a two way valve 54. The bottom port 56 is adapted to be coupled to a source of pressurized air (not shown) while the top port 57 is coupled to a conventional vacuum pressure measuring guage 58. A control lever 59 is coupled to the outlet 90 for controlling the flow of air as is well known in the art.

Figure 7:
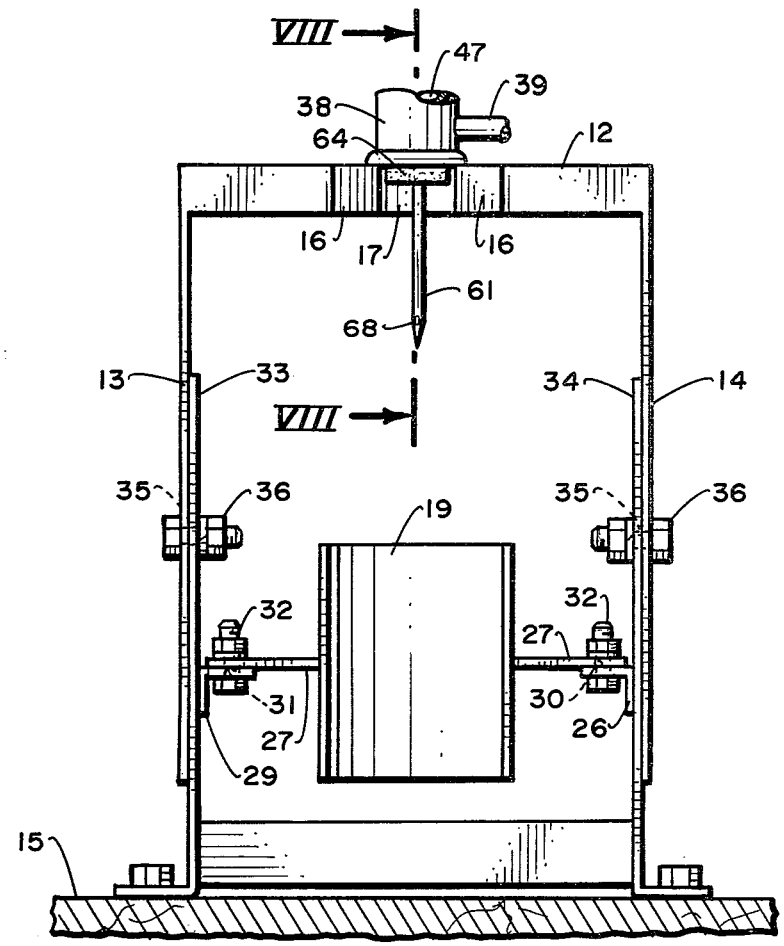
FIG. 7 is a detailed vertical front view of a portion of the apparatus of FIG. 1 showing the needle in piercing position.
Figure 8:
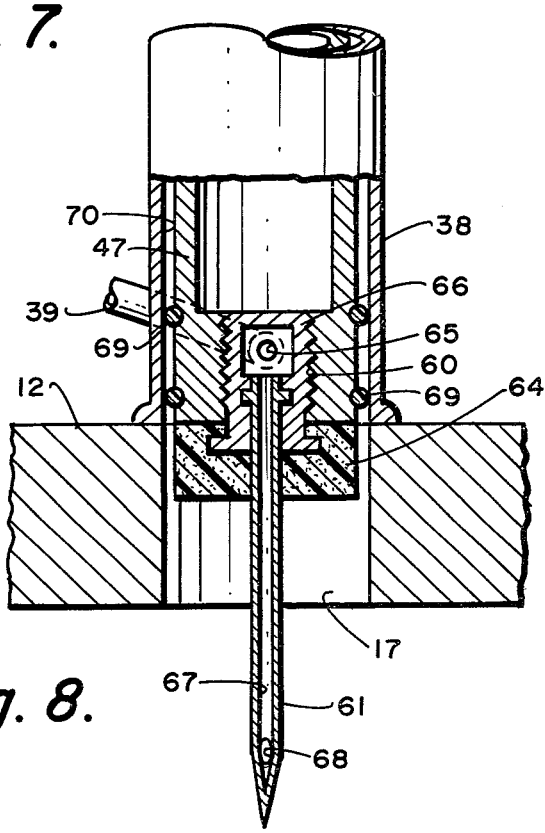
FIG. 8 is a detailed cross-sectional view taken along lines VIII—VIII of FIG. 7 of the piston, cylinder and needle of the invention.

As shown in FIGS. 7 and 8, the bottom of piston 47 terminates in a threaded socket 60 receiving therein a threaded fitting 66 connected to a rubber collar 64 having a downwardly extending cork piercing needle which is also fluidly connected via suitable air conduit 65 to gauge 58. Needle 61 is hollow and it is to be understood that movement of lever 40 moves needle 61 up or down to pierce the corks of successive bottles in housing 11. The bottom of cylinder 38 may be securely held in position on top wall 12 at slot 16 in any suitable manner, such as by welding, as long as needle 61 is aligned with substantially the center of the cork of the bottle to be pierced. Needle 61 has a longitudinal opening 67 communicating at one end with port 65 and at the other end with needle eye 68. Piston 47 may also have one or more C-rings 69 slidably enaging the inner wall 70 of cylinder 38 as is well known in the art.

The operation of the apparatus 10 of FIG. 1 is clearly shown in FIGS. 9 and 10. A bottle 63 is placed within housing 11 abutting against support 19 with the neck thereof entering apex 17 thus aligning the cork in the bottle with the path of travel of the piercing needle 61. Of course, support 19 and wall panels 33,34 are adjusted, if necessary, to accomodate the bottle shape and size, as previously discussed. Needle 61 is or course internally of cylinder 38 since lever 40 is in the up or FIG. 9 position. As shown in FIG. 10, movement of lever 40 downwardly to the FIG. 10 position allows needle 61 to pierce the cork in the bottle 63 thus entering the air space between the bottom of the cork and the upper level of liquid in the bottle thereby permitting any air present in bottle 63 to enter the eye 68 of needle 61 and exit via opening 67 to air inlet 39. The gauge 58 measures the psi of the air in the bottle since needle 61 is directly connected to guage 58 via eye 68 and opening 67.

The valve 54 permits a source of air to be connected to inlet 57 to blow air out of the needle to keep cork dust or the like from plugging the needle 61.

It can be seen that apparatus 10 can use a relatively small needle 61 to penetrate the cork since the apparatus is designed to deliver a straight linear downward force.

The threaded connection between needle 61 and piston 47 allows the needle 61 to be quickly and easily replaced when necessary.

The relatively easy vertical and horizontal adjustment of support 19 and top wall 12 allows the apparatus to accomodate various sized bottles so needle 61 can be aligned with the center of the cork. The curvature of slot 16 thus raises to interface with the bottle top.

The two way valve 54 permits gauge 58 to be closed off when air is introduced for cleaning to avoid breakage when blowing air through inlet 39 and through needle 61 out the eye thereof to clean the same. Guage or meter 58 is preferably adapted only to measure relatively low p.s.i., e.g., 15 p.s.i., since pressurized gas or air usually on hand at wineries may be of a relatively higher p.s.i. Thus, protection via valve 54 is necessary so that such higher pressures may be used.

Support for the bottle can be provided by means other than curved support 19. For example, a flat plate may be substituted with suitable stops or guides, such as rubber pads, provided thereon.

Any suitable materials may be used, such as brass, for the cylinder 38 and various fittings. Any suitable dimensions may be used, such as needle 61 having an O.D. of between about 0.125 to 0.150 inches and a stroke or piercing length of between about 2.25 to 2.75 inches. The needle eye 68 may be about 0.004 inches and the central opening in the needle may be about 0.0032 inches. Needle 61 may be of polished steel. Although needle 61 has been described as having a single eye 68 communicating with opening 67, it may have a plurality, such as three.

It can be seen that we have described an improved apparatus for piercing the cork of a bottle and detecting the pressure of air therein. Also, if desired, a small amount of liquid may be removed for sampling from the bottle merely by adjusting the position of the bottle on the apparatus 10.

The meter or guage 58 may be of any suitable type, such as one adapted to read from 0 to 15 p.s.i. on one hand or 0 to 30 inches of mercury on the vacuum side. It may include a guage needle lock, if desired.

The apparatus disclosed herein may be used in other wine making processes, such as extracting wine and checking into sugar content and taking oxygen readings.

It can also be seen that I have disclosed improved apparatus for quickly and easily determining the presence of air to corked bottles of wine or the like.

An optional plastic bumper, not shown, may be employed on the underside of apex 17 to reduce impact of the bottle with said apex which is metallic.

Figure 11:
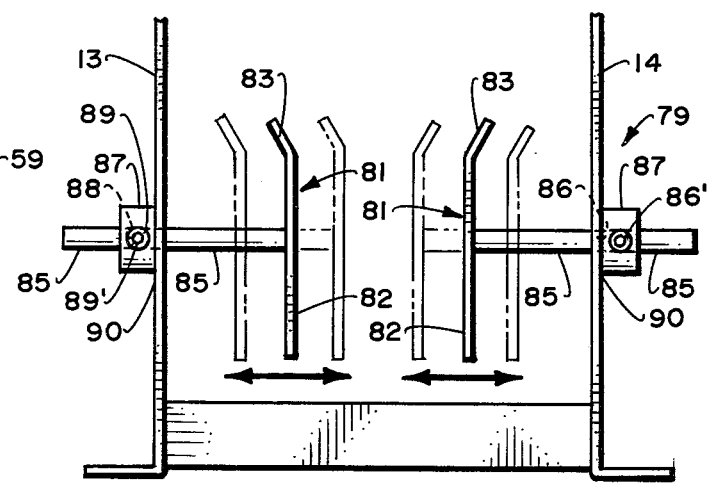
FIG. 11 is a front perspective view of an alternate version of one portion of the invention.

In addition to the structure just discussed, I have also invented an alternate version to one portion of the invention. That is, the bottle guide noted as 19 above. The reader's attention is now turned to FIG. 11. Bottle support 19 is replaced by bottle guide 79. This comprises a pair of spaced bottle retainers 81 which may be either straight or slightly arcuate horizontally, each of which includes a vertical major portion 82 nand an angled minor portion 83 diverging outwardly from the top edge of the major portion. Connected at about the midpoint of the major portion, normal thereto, is adjusting arm 85. This may be secured by welding or by suitable bolts not shown. Arm 85 extends through horizontally aligned aperture 86 in side wall 13, while the corresponding arm 85 on the opposite side extends through corresponding aperture 86' on the opposite side wall 14.

Collar 87 having an aligned horizontal throughbore 88 is mounted on its front face 90 to the outside surface of the respective side walls 13 and 14. Arm 86 extends through said throughbore and beyond the width of the collar a suitable amount to provide adeqiate support and counterbalance for the bottle retainer 81 such that it will not tip over angularly. Collar 87 includes a threaded bore 89' horizontal to the first mentioned bore 88 that extends from the exterior surface of the collar to the throughbore. Disposed within the threaded bore 89' is thumbscrew 89 which upon tightening will seat itself upon arm 85 to retain said arm at a desired position. Though not shown, if desired arm 85 can be scribed with indicia corresponding to bottle size.

Each of the two halves of guide 79 is adjusted independently according to bottle diameter. By being able to adjust each side independently, one can test odd shaped decanters, similar to those used by Jim Beam for the bottling of alcoholic beverages, as well as other decanters where the neck and bottle opening are off center.

When carrying out the test procedure it is necessary first to clear the needle of pre-existing wine from a just completed test, one of several modes may be employed. Valve handle 59 is opened such that access can be had through front port 91. A spray of ethanol is injected into the valve body through this port and down into the needle to remove the prior wine.

Alternatively, a blast of air is inserted through port 56 back to the needle to remove any wine or foreign body, i.e., cork remmant. This latter is the easier cleaning mode. This is readily achievable since the valve is a three way valve. On employing either flush system, no alcohol or air reaches the meter (gauge) which is closed off.

After the bottle cork is pierced and the necessary sample is withdrawn during the test procedure, the balance of the bottle's content is reprocessed. Generally it is mixed with lower grade wines for non-vertical bottlings. Sulfur may be added as is known in the art to kill any bacteria that may have entered the bottle through the puncture. The removal of such sulphur is also known in the art.

While a standard analog meter is shown in the figures, it is recognized that a digital readout can be equally employed with the same results.

We claim:

1. Apparatus for piercing a cork sealing off the neck of a bottle adapted to contain a liquid therein comprising:
   a housing having guide means thereon for receiving a bottle and aligning said bottle so that said bottle is disposed in an upright position with the cork sealing off the neck of said bottle having its upper surface exposed to the atmosphere wherein said guide means includes a top wall on said housing having a tapered slot therein for receiving the neck of a bottle;
   a cylinder having an internal movable piston therein disposed on said housing above said guide means, said piston carrying a downwardly extending hollow cork piercing needle having an eye at the lower end fluidly communicating with a longitudinally extending opening therein and its longitudinal axis aligned with substantially the center of said cork upper surface, said piston being movable from a first position whereby the point of said needle is disposed above the upper surface of said cork to a second position whereby said needle pierces said cork and the eye thereof enters said bottle below the lower surface of said cork; and including a handle pivotally connected to said cylinder having linkage means interconnecting said handle to said piston whereby said piston is movable between its first and second positions by pivotal movement of said handle.

2. In the apparatus of claim 1 including air pressure detecting means fluidly coupled to the longitudinal opening in said needle for detecting the presence of any air passing from said bottle into the eye of said needle, through said longitudinal opening therein and to said air pressure detecting means.

3. In the apparatus of claim 2 wherein said detecting means includes a port in said cylinder in fluid communication with the longitudinal opening in said needle, a valve fluidly coupled to said port, and a pressure measuring guage coupled to said valve.

4. In the apparatus of claim 3 wherein said valve includes a normally closed threaded fitting in fluid communication with said port adapted to be coupled to a source of pressurized fluid and a valve control lever coupled to said valve for selectively closing off said threaded fitting from fluid communication with said guage and said port or opening said port to said guage while closing off said threaded fitting from fluid communication with said guage and said port.

5. In the apparatus of claim 1 wherein said needle is removably connected to said piston.

6. In the apparatus of claim 5 wherein said needle is threadably connected to said piston by a threaded fitting threading into a socket on said piston, a port on said fitting fluidly communicating with said longitudinal opening in said needle.

7. In the apparatus of claim 1 wherein said guide means further includes said top wall being vertically adjustable so that the overall height of said slot may be varied to accomodate bottles of varying heights.

8. In the apparatus of claim 1 wherein said guide means further includes an abutment plate on said housing below said slot and plate adjusting means on said housing engaging said plate for adjusting the horizontal position of said plate with respect to said housing.

9. In the apparatus of claim 8 wherein said plate adjusting means further includes means for adjusting the vertical position of said plate with respect to said housing.

10. In the apparatus of claim 8 wherein said abutment plate includes a curved plate curving concavely inwardly toward a vertical line passing downwardly through said slot.

11. Apparatus as in claim 1 wherein the bottle guide means for receiving the bottle and aligning same, comprises a pair of spaced vertical bottle retainers, each having an adjusting arm mounted thereon,
   a collar mounted on the exterior of the side wall of the apparatus, said collar having a throughbore that communicates with and is in alignment with an aperture in said side wall,
   said arm extending through said sidewall bore and said collar throughbore,
   adjustable position securing means within said collar to prevent movement of said arm within said throughbore after a desired location has been set for said arm.

* * * * *